United States Patent [19]

Benko et al.

[11] Patent Number: 5,602,075
[45] Date of Patent: Feb. 11, 1997

[54] N-ARYL[1,2,4]TRIAZOLO[1,5-A]PYRAZINE-2-SULFONAMIDE HERBICIDES

[75] Inventors: Zoltan Benko, Indianapolis; John J. Jachetta, Zionsville; Mark J. Costales; Kim E. Arndt, both of Indianapolis, all of Ind.

[73] Assignee: DowElanco, Indianapolis, Ind.

[21] Appl. No.: 273,258

[22] Filed: Jul. 11, 1994

[51] Int. Cl.$^6$ .................................................. A01N 43/653
[52] U.S. Cl. ........................................ 504/235; 548/262.4
[58] Field of Search ............................ 548/262.4, 267.2; 504/235

[56] References Cited

U.S. PATENT DOCUMENTS

| | | | |
|---|---|---|---|
| 4,605,433 | 8/1986 | Pearson et al. | 71/93 |
| 4,795,483 | 1/1989 | Gates et al. | 71/90 |
| 4,818,273 | 4/1989 | Kleschick et al. | 71/90 |
| 4,889,553 | 12/1989 | Rowson et al. | 71/92 |
| 5,163,995 | 11/1992 | Van Heertum et al. | 71/92 |
| 5,201,938 | 4/1993 | Costales et al. | 504/241 |

FOREIGN PATENT DOCUMENTS

| | | |
|---|---|---|
| 244948 | 11/1987 | European Pat. Off. . |
| 419831 | 8/1990 | European Pat. Off. . |

*Primary Examiner*—Brian M. Burn
*Attorney, Agent, or Firm*—D. Wendell Osborne

[57] ABSTRACT

Substituted N-aryl[1,2,4]triazolo[1,5-a]-pyrazine-2-sulfonamide compounds, such as 5-bromo-N-(2,6-dichlorophenyl)-8-methoxy[1,2,4]triazolo[1,5-a]-pyrazine-2-sulfonamide, were prepared by condensation of a substituted 2-chlorosulfonyl[1,2,4]triazolo[1,5-a]pyrazine compound, such as 5-bromo-2-chlorosulfonyl-8-methoxy[1,2,4]triazolo[1,5-a]pyrazine with a substituted arylamine compound, such as 2,6-dichloroaniline, and found to possess herbicidal utility.

21 Claims, No Drawings

N-ARYL[1,2,4]TRIAZOLO[1,5-A]PYRAZINE-2-SULFONAMIDE HERBICIDES

BACKGROUND OF THE INVENTION

The present invention relates to substituted sulfonamide compounds, to herbicidal compositions containing the compounds, and to the utility of the compounds for the control of unwanted vegetation.

The control of unwanted vegetation by means of chemical agents, i.e. herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment are less expensive to use, or have other advantageous attributes are desirable.

A number of sulfonamide compounds, including certain substituted [1,2,4]triazolo[1,5-a]pyrimidine-2-sulfonamide compounds (U.S. Pat. No. 4,954,163) and [1,2,4]triazolo[1,5-c]pyrimidine-2-sulfonamide compounds (U.S. Pat. No. 5,010,195 and European Application 244,948), are known and are known to possess herbicidal activity, especially on broadleaf weeds.

SUMMARY OF THE INVENTION

It has now been found that certain N-aryl-[1,2,4]triazolo[1,5-a]pyrazine-2-sulfonamide compounds are potent herbicides for the control of unwanted vegetation, have desirable crop selectivity, and have favorable toxicological and environmental attributes.

The invention includes N-aryl[1,2,4]triazolo-[1,5-a]pyrazine-2-sulfonamide compounds of Formula I:

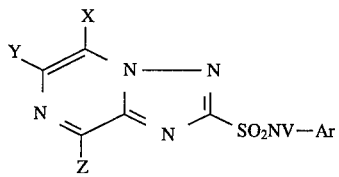

wherein

X, Y, and Z each independently represents H, $CH_3$, $CF_3$, F, Cl, Br, or $(C_1–C_3)$alkoxy;

V represents H, COR', $CO_2R''$, or $CONR'''_2$;

Ar represents an aromatic moiety of one of the formulas:

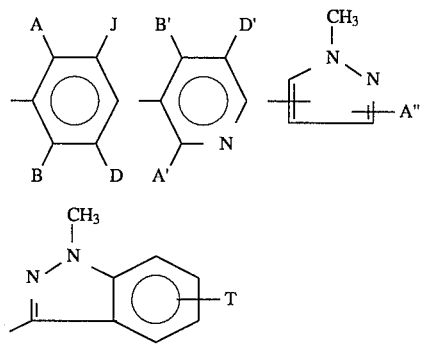

A represents F, Cl, Br, $CO_2R''$, $CONR'''_2$, $(C_1–C_2)$haloalkyl, $NO_2$, CN, SOR', or $SO_2R'$;

B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$ and $CH_3$;

D and J each independently represents H or $CH_3$ with the proviso that at least one of D and J represents H;

A' and B' each independently represents H, R', OR', $S(O)_nR'$, F, Cl, Br, I, CN, $NO_2$, $C_6H_5$, $CO_2R''$, or $CONR'''_2$ with the proviso that not more than one of A' and B' represents H;

D' represents H, F, Cl, Br, I, $CF_3$, or $CH_3$;

A" represents F, Cl, Br, I, $CF_3$, $SCF_3$, CN, $CO_2R''$, or $CONR'''_2$ and is located in the 4-position when the point of attachment is the 3- or 5-position and represents F, Cl, Br, I, $CF_3$, or $CH_3$ and is located in the 3- and/or 5-position when the point of attachment is the 4-position;

T represents H or F;

n represents 0, 1, or 2;

R' represents $(C_1–C_3)$alkyl optionally singly to completely substituted with fluorine;

R" represents $(C_1–C_4)$alkyl, $(C_3–C_4)$alkenyl, or $(C_3–C_4)$alkynyl;

R'" represents H or $(C_1–C_4)$alkyl; and when V represents H, the agriculturally acceptable salts thereof.

The compounds of the invention, usually in the form of an herbicidal composition containing one or more of them in admixture with an agriculturally acceptable adjuvant or carrier, exhibit strong herbicidal properties when applied either directly to the unwanted vegetation or to the locus thereof and when applied either preemergence or postemergence.

DETAILED DESCRIPTION OF THE INVENTION

The novel herbicidal compounds of the invention are N-aryl[1, 2, 4]triazolo[1,5-a]pyrazine-2-sulfonamide compounds of Formula I:

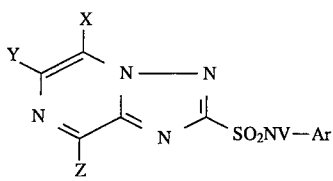

These compounds can be described as amides derived from [1,2,4]triazolo[1,5-a]pyrazine-2-sulfonic acid compounds and substituted aromatic amine compounds. The Chemical Abstracts nomenclature numbering system for [1,2,4]triazolo[1,5-a]pyrazine ring compounds is as follows:

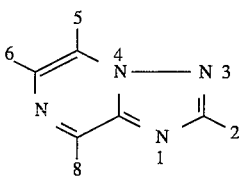

Thus, the compounds of the invention are 2-sulfonamide compounds and the X substituents are in the 5-position, the Y substituents are in the 6-position, and the Z substituents are in the 8-position.

The compounds of the invention include those of Formula I wherein X, Y, and Z each independently represents hydrogen, lower alkyl, fluorinated lower alkyl, halo, or lower alkoxy. The substituents H, $CH_3$, $CF_3$, F, Cl, Br, and $(C_1-C_3)$alkoxy are specifically identified. It is usually preferred that one or both of X and Z represents methoxy or ethoxy.

The compounds of the invention further include those of Formula I wherein V represents hydrogen, an acyl moiety, a hydrocarbyloxycarbonyl, or a carbamoyl moiety. Such compounds wherein V represents H, COR', $CO_2R''$, or $CONR'''_2$ and R' represents $(C_1-C_3)$alkyl optionally singly to completely substituted with fluorine, R'' represents $(C_1-C_4)$alkyl, $(C_3-C_4)$alkenyl, or $(C_3-C_4)$alkynyl, and R''' represents H or $C_1-C_4$ alkyl are specifically identified. When V represents hydrogen, the compounds of Formula I are acidic and the invention includes the agriculturally acceptable salts of these acids. Compounds of Formula I wherein V represents hydrogen are generally preferred.

The term Ar in Formula I represents an aromatic moiety, especially an aromatic moiety of one following formulas:

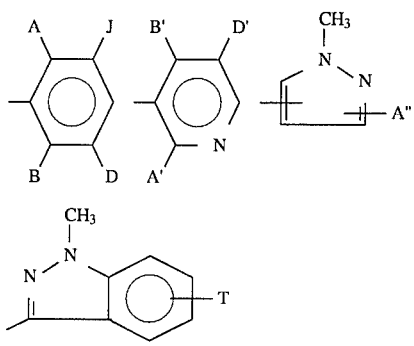

which includes phenyl moieties, 3-pyridinyl moieties, 1-methyl-(3-, 4-, or 5-)pyrazolyl moieties, and 1-methyl-3-indazolyl moieties.

When Ar represents a phenyl moiety, the moiety is substituted in at least one ortho position with an electron withdrawing group. Compounds of Formula I wherein Ar represents a substituted phenyl moiety include those wherein A represents F, Cl, Br, $CO_2R''$, $CONR'''_2$, $(C_1-C_2)$haloalkyl, $NO_2$, CN, SOR', or $SO_2R'$; B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$, and $CH_3$; and D and J each independently represents H or $CH_3$ with the proviso that at least one of D and J represents H. Compounds wherein A represents one of F, Cl, Br, $CO_2R''$, $NO_2$, and $CF_3$; B represents one of F, Cl, Br, $OCH_3$, and $CH_3$; J represents H, and D represents H or $CH_3$ are often preferred. Compounds wherein A and B both represent F or Cl and D and J both represent H, wherein A and B both represent F or Cl, D represents $CH_3$, and J represents H, wherein A represents $CO_2CH_3$, B represents Cl or F, and D and J both represent H, and wherein A represents $CF_3$, B represents $OCH_3$, and D and J both represent H are often more preferred.

When Ar represents a 3-pyridinyl moiety, the moiety is substituted in at least one of the 2- and 4-positions. Compounds of Formula I wherein Ar represents a substituted 3-pyridinyl moiety include those wherein A' and B' each represents H, F, Cl, Br, I, CN, $NO_2$, $C_6H_5$, $CO_2R''$, or $CONR'''_2$, or $(C_1-C_3)$alkyl, $(C_1-C_3)$alkoxy, $(C_1-C_3)$alkylthio, $(C_1-C_3)$alkylsulfinyl, or $(C_1-C_3)$alkylsulfonyl each optionally singly to completely substituted with fluorine, and D' represents H, F, Cl, Br, I, $CF_3$, or $CH_3$. Such compounds wherein A' represents Cl, F or $OCH_3$; B' represents $CH_3$, $OCH_3$, $OC_2H_5$, or $OC_3H_7$; and D' represents H or wherein A' represents H; B' represents $CO_2(C_1-C_2)$alkyl; and D' represents H are typically preferred. 3-Pyridinyl moieties wherein B' represents $CH_3$, A' represents F, and D' represents H and wherein B' represents $OCH_3$ or $OC_2H_5$, A' represents Cl, and D' represents H are often more preferred.

When Ar represents a pyrazolyl moiety, the moiety is attached to the sulfonamide nitrogen atom at a 3-, 4-, or 5-position and has a methyl group in the 1-position. When the point of attachment is the 3- or 5-position, the moiety is substituted in the 4-position with an electron withdrawing group. The 3- or 5-position attachment compounds wherein the 4-position substituent A'' represents F, Cl, Br, I, $CF_3$, $SCF_3$, CN, $CO_2R''$, or $CONR'''_2$ are specifically identified. Those wherein A'' represents Cl, Br, I, or $CF_3$ are usually preferred. When the point of attachment is the 4-position, the moiety is substituted in the 3- or 5-position. Such compounds wherein the 3- and/or 5-position substituent A'' represents F, Cl, Br, I, $CF_3$, or $CH_3$ are specifically identified. Those wherein A'' represents Cl, Br, I, or $CF_3$ are usually preferred.

When Ar represents an indazolyl moiety, the moiety is attached to the sulfonamide nitrogen atom at the 3-position, has a methyl group in the 1-position, and is optionally mono-substituted with fluorine. Such compounds having a fluoro substituent in the 4-position are often preferred.

The term alkyl as used herein includes straight chain, branched chain, and cyclic moieties. Thus, typical alkyl groups are methyl, ethyl, 1-methylethyl, propyl, cyclopropyl and the like. Methyl and ethyl are often preferred. Typical alkyl groups singly to completely substituted with fluorine include trifluoromethyl, monofluoromethyl, 2,2,2-trifluoroethyl, 2,3-di-fluoropropyl, and the like; trifluoromethyl is often preferred. The term haloalkyl is used herein to denote alkyl singly to completely substituted with fluorine or chlorine and includes trifluoromethyl, dichloromethyl, 2,2-difluoro-2-chloroethyl, and the like; trifluoromethyl is often preferred. The terms halo and halogen include fluorine, chlorine, bromine, and iodine.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$R^6R^7R^8NH^{\oplus}$ wherein $R^6$, $R^7$, and $R^8$ each, independently represents hydrogen or $(C_1-C_{12})$alkyl, $(C_3-C_{12})$cycloalkyl, or $(C_3-C_{12})$alkenyl, each of which is optionally substituted by one or more hydroxy, $(C_1-C_8)$alkoxy, $(C_1-C_8)$alkylthio or phenyl groups; provided that $R^6$, $R^7$, and $R^8$ are sterically compatible. Additionally, any two of $R^6$, $R^7$, and $R^8$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

A listing of some typical compounds of the invention is given in Table 1. Some of the specifically preferred compounds of the invention include the following:

5-bromo-N- (2,6-dichlorophenyl)-8-methoxy [1,2,4]triazolo-[1,5-a]pyrazine-2-sulfonamide, 5-bromo-N-(2-fluoro-6-methoxycarbonylphenyl)-8-methoxy[1,2,4] triazolo[1,5 -a]pyrazine-2-sulfonamide, N-(2,6-dichlorophenyl) -5,8-dimethoxy-[1,2,4]triazolo[1,5-a]pyrazine-2-sulfonamide, 6-chloro-N-(2,6 -dichlorophenyl)-8-methoxy [1,2,4]triazolo[1,5-a]-pyrazxine-2-sulfonamide, and 6-chloro-N-(2,6-difluorophenyl)-8-methoxy[1,2,4]triazolo[1,5 -a]pyrazine-2-sulfonamide and the agriculturally acceptable salts thereof.

TABLE 1

N-ARYL[1,2,4]TRIAZOLO[1,5-A]PYRAZINE-2-SULFONAMIDE COMPOUNDS

| Cpd. No. | X | Y | Z | Ar | Form | Melting point, °C. | % C calc. found | % H calc. found | % N calc. found |
|---|---|---|---|---|---|---|---|---|---|
| 1 | H | H | H | 2,6-dichlorophenyl | white crystals | 194–196 | 38.5 38.9 | 2.42 2.44 | 18.7 18.5 |
| 2 | Br | H | H | 2,6-dichlorophenyl | light brown solid | 245(d) | 31.2 33.3 | 1.43 1.77 | 16.6 16.0 |
| 3 | OCH$_3$ | H | H | 2,6-dichlorophenyl | pale yellow powder | 214–215 (d) | 38.5 38.9 | 2.42 2.67 | 18.7 18.4 |
| 4 | OCH$_3$ | H | H | 2,6-difluorophenyl | yellow powder | 180(d) | 42.3 42.1 | 2.64 2.85 | 20.5 20.0 |
| 5 | OCH$_3$ | H | H | 2-fluoro-6-methoxy-carbonylphenyl | tan powder | 170(d) | 44.1 43.8 | 3.17 3.18 | 18.4 18.1 |
| 6 | OC$_2$H$_5$ | H | H | 2,6-dichlorophenyl | pale yellow powder | 215–216 (d) | 40.2 39.8 | 2.84 3.06 | 18.0 17.3 |
| 7 | OC$_2$H$_5$ | H | H | 2,6-difluorophenyl | pale yellow powder | 203–204 (d) | 43.9 44.1 | 3.12 3.20 | 19.1 19.4 |
| 8 | H | H | CH$_3$ | 2,6-dichlorophenyl | pale yellow solid | 224–225 | 40.2 40.2 | 2.53 2.41 | 19.6 19.3 |
| 9 | H | H | CH$_3$ | 2,6-difluorophenyl | pale yellow powder | 205–206 | 44.3 44.2 | 2.79 2.90 | 21.5 21.3 |
| 10 | H | H | OCH$_3$ | 2,6-dichlorophenyl | white powder | 244–246 | 38.5 38.7 | 2.42 2.75 | 18.7 18.5 |
| 11 | H | H | Cl | 2,6-dichlorophenyl | white powder | 237–238 | 34.9 35.1 | 1.60 1.82 | 18.5 18.2 |
| 12 | Br | H | Br | 2,6-dichlorophenyl | light yellow solid | 249–250 (d) | 26.3 28.5 | 1.00 1.26 | 14.0 13.7 |
| 13 | Br | H | OCH$_3$ | 2,6-dichlorophenyl | white powder | 269–271 | 31.8 32.1 | 1.78 1.87 | 15.5 15.3 |
| 14 | Br | H | OCH$_3$ | 2,6-difluorophenyl | off-white powder | 265 (d) | 34.3 34.2 | 1.92 1.96 | 16.7 16.9 |
| 15 | Br | H | OCH$_3$ | 2-fluoro-6-methoxy-carbonylphenyl | lt. tan powder | 201–202 | 36.5 36.6 | 2.41 2.39 | 15.2 14.9 |
| 16 | OCH$_3$ | H | OCH$_3$ | 2,6-dichlorophenyl | white powder | >250(d) | 38.6 38.2 | 2.74 2.88 | 17.3 16.8 |
| 17 | H | Cl | OCH$_3$ | 2,6-dichlorophenyl | light purple powder | 254–255 | 35.3 35.3 | 1.97 1.90 | 17.1 17.1 |
| 18 | H | Cl | OCH$_3$ | 2,6-difluorophenyl | off-white powder | 233–234 | 38.4 38.4 | 2.15 2.04 | 18.6 18.6 |
| 19 | H | Br | OCH$_3$ | 2,6-difluorophenyl | off-white solid | 226–227 | 34.3 34.8 | 1.92 1.67 | 16.7 16.2 |
| 20 | Br | H | OCH$_3$ | 2-fluoro-4-methyl-3-pyridinyl | light yellow powder | 234–237 (d) | 34.5 34.8 | 2.42 2.21 | 20.1 20.0 |
| 21 | H | Cl | OCH$_3$ | 2-fluoro-4-methyl-3-pyridinyl | tan powder | 228–230 | 38.7 38.2 | 2.70 2.81 | 22.5 21.7 |
| 22 | H | Br | OCH$_3$ | 2-fluoro-4-methyl-3-pyridinyl | pale yellow | 210–211 (d) | 34.6 34.5 | 2.42 2.56 | 20.1 18.4 |

TABLE 1-continued

N-ARYL[1,2,4]TRIAZOLO[1,5-A]PYRAZINE-2-SULFONAMIDE COMPOUNDS

| Cpd. No. | X | Y | Z | Ar | Form | Melting point, °C. | % C calc. found | % H calc. found | % N calc. found |
|---|---|---|---|---|---|---|---|---|---|
| 23 | Br | H | OCH₃ | 1-methyl-4-bromo-5-pyrazolyl (85%, 15% 4-chloro) | powder pale yellow solid | d | 25.7 25.3 | 1.94 2.31 | 21.0 19.7 |
| 24 | H | Cl | OCH₃ | 1-methyl-4-bromo-5-pyrazolyl | tan powder | 236–237 | 28.4 29.8 | 2.15 2.08 | 23.2 21.5 |
| 25 | H | Br | OCH₃ | 1-methyl-4-bromo-3-pyrazolyl | lt. tan solid | 238–239 | 25.7 24.9 | 1.94 1.26 | 21.0 20.1 |
| 26. | Br | H | Br | 2,6-difluorophenyl | off-white powder | d | 28.2 29.4 | 1.07 1.03 | 14.7 14.9 |
| 27. | Br | H | Br | 2-fluoro-6-methoxy-carbonylphenyl | orange glassy solid | 190–195 | 30.7 31.6 | 1.58 1.49 | 13.8 13.8 |
| 28 | Br | H | Cl | 2,6-dichlorophenyl | fluffy white solid | d | 28.9 30.3 | 1.10 1.21 | 15.3 14.8 |

The compounds of Formula I wherein V represents hydrogen can generally be prepared by combining a 2-chlorosulfonyl[1,2,4]triazolo[1,5-a]pyrazine compound of Formula II:

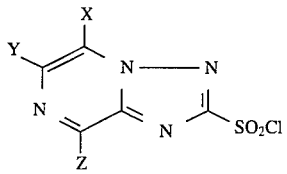

with an appropriately substituted aromatic amine compound selected from the following formulas:

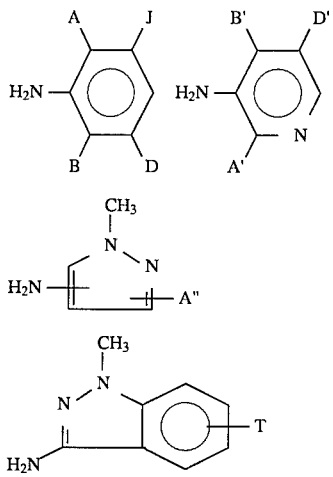

in the presence of pyridine or a methylpyridine compound, and, optionally but preferably, a catalytic amount of dimethyl sulfoxide. The substituents X, Y, and Z of Formula II and the substituents A, B, D, J, A', B', D', A", and T of the aromatic amine compounds are as defined hereinabove.

The preparation is usually accomplished by placing the 2-chlorosulfonyl[1,2,4]triazolo[1,5-a]pyrazine compound of Formula II, the aromatic amine, and an inert solvent, such as acetonitrile, N,N-dimethylformamide, N-methyl-2-pyrrolidinone, tetrahydrofuran, and the like, in a vessel and then adding the pyridine or methylpyridine, preferably pyridine, and a catalytic amount of dimethyl sulfoxide. The mixture is allowed to react, typically at ambient temperature, but heating if necessary. After a substantial quantity of the compound of Formula I has formed or a substantial quantity of the sulfonyl chloride compound of Formula II has been consumed, the desired product is recovered, typically by removing the solvent by evaporation, adding water, and removing the liquids from the solid that forms by filtration or centrifugation. The recovered product can be purified, if desired, by extracting with an immiscible organic solvent, such as methylene chloride, and with water. Alternatively, the desired compounds of Formula I can be purified by recrystallization and by other commonly used methods.

Approximately equimolar quantities of the compound of Formulas II and the aromatic amine are generally used in the preparation of compounds of Formula I, although a substantial excess of one or the other may be employed. Small to large excesses of the aromatic amine compound are sometimes helpful. The pyridine compound is generally employed in an amount of from at least 1 to about 5 moles per mole of compound of Formula II. Dimethyl sulfoxide is typically used in less than an equimolar amount; amounts over about 0.3 mole per mole of compound of Formula II are usually deleterious. Acetonitrile is often the preferred solvent.

It is sometimes advantageous to prepare the compounds of Formula I by condensing a compound of Formula II with an N-trialkylsilyl derivative of the aromatic amine compound. The method employed is analogous to that described in U.S. Pat. No. 4,910,306 for N-trialkylsilylanilines. The reaction conditions required are essentially the same as those described hereinabove for the condensation of a compound of Formula II with an aromatic amine with the exception that the pyridine compound base may be omitted. An aqueous work-up procedure is typically employed. The substituted N-trialkylsilyl derivatives of the aromatic amine compounds employed can be prepared from the corresponding aromatic amine compounds by treatment with a trialkylsilyl halide and a trialkylamine as described in U.S. Pat. No. 4,910,306 for aniline compounds. Sodium iodide is typically employed as a catalyst when the halide is chloride. The N-trialkylsilylamine compounds are typically prepared and used immediately and without purification.

Compounds of Formula I wherein V represents hydrogen and one or both of X and Z represent alkoxy or alkylthio and can be prepared from the corresponding compounds of Formula I wherein X and/or Z represents Cl or Br by treatment with an appropriate nucleophilic reagent, such as sodium methoxide or sodium methanethiolate in methanol. The reaction conditions employed are similar to those used for the related exchange reactions of 2-chloropyrazines. Non-aqueous media are preferred. Selective replacement of a halogen in the Z position can readily be achieved as a halogen in this position is much more reactive than a halogen in the X position.

Compounds of Formula I wherein X represents alkoyl, Y represents hydrogen, and Z represents chloro can be prepared from compounds of Formula I wherein X represents alkoxy and Y and Z represent hydrogen by treatment with hydrogen peroxide in trifluroacetic acid at a temperature of about 0° to 80° C. to obtain the 7-position N-oxide derivative. This intermediate compound is then treated with phosphorus oxychloride in a solvent, such as acetonitrile, at a temperature of about 50° to about 100° C.

Compounds of Formula I wherein V represents COR', $CO_2R''$, or $CONR'''_2$ (R' represents $(C_1-C_3)$alkyl optionally singly to completely substituted with fluorine, R" represents $(C_1-C_4)$alkyl, $(C_3-C_4)$alkenyl, or $(C_3-C_4)$alkynyl, and R''' represents H or $(C_1-C_4)$alkyl) can be prepared from compounds of Formula I wherein V represents hydrogen by acylation with a compound of the formula ClCOR', $ClCO_2R''$, or $ClCONR'''_2$, respectively, using conventional procedures known in the art for the acylation of sulfonamides.

The 2-chlorosulfonyl[1,2,4]triazolo[1,5-a]pyrimidine compounds of Formula II can be prepared by chloroxidation of the corresponding compound of Formula III wherein X, Y, and Z are as defined hereinbefore:

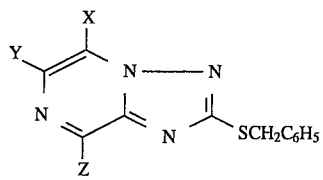

The benzyl compound dissolved in an inert solvent, such as dichloromethane, is treated with an excess (more than 3 moles per mole of benzylthio compound) of sodium hypochlorite in aqueous hydrochloric acid at about 0° C. and, after the reaction is complete, the organic phase is separated and the compound of Formula II is recovered from it by conventional means. The sulfonyl chlorides were typically not purified before further use. This process is particularly of value for compounds wherein at least one of X, Y, and Z represents fluoro, chloro, or bromo.

Some of the substituted aniline, 3-aminopyridine, 3-, 4-, and 5-aminopyrazole, and 3-aminoindazole compounds that are required as intermediates for the compounds of Formula I are known in the art or can be prepared by the general methods known in the art. Other such compounds can be prepared by the methods of the Examples and by conventional modifications thereof readily apparent to those of ordinary skill in the art.

While it is possible to utilize the [1,2,4]triazolo[1,5-a]pyrazine-2-sulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonire clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethorylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include antifoam agents, compatibilizing agents, sequestering agents, neutralizing agents and buffers, corrosion inhibitors, dyes, odorants, penetrations aids, spreading agents, sticking agents, dispersing agents, thickening agents, freeze point depressants, antimicrobial agents, and the like. The compositions can also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence and postemergence herbicides. They can be employed at non-selective (higher) rates of application to control essentially all of the vegetation in an area and, often, at selective (lower) rates of application for the selective control of undesirable vegetation in grass crops, such as corn, wheat, barley, and rice as well as in broadleaf crops, such as soybeans and cotton. While each of the N-aryl[1,2,4]triazolo-[1,5-a]pyrazine-2-sulfonamide compounds encompassed by Formula I is within the scope of the invention, the degree of herbicidal activity, the selectivity, and the spectrum of weed control obtained varies depending upon the substituents present.

The term herbicide is used herein to mean an active ingredient which controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature plants to achieve the maximum control of broadleaf weeds.

Application rates of about 0.001 to about 1 Kg/Ha are generally employed in postemergence operations; for preemergence applications, rates of about 0.01 to about 10 Kg/Ha are generally employed. The higher rates designated generally give non-selective control of a broad variety of undesirable vegetation. The lower rates typically give selective control and, by judicious election, can be employed in the locus of crops.

EXAMPLES

The following Examples are presented to illustrate the various aspects of this invention and should not be construed as limitations to the claims.

1. Preparation of Imidazol-1-yl-N-(2-amino-1-pyrazinium) Iminocarbothiolate.

A suspension of 1.90 g (grams) of 1, 2-diaminopyrazinium mesitylenesulfonate was prepared in 40 mL (milliliters) of chloroform and to this was added 1.50 g of 90 percent purity 1,1'-thiocarbonyldiimidazole with stirring at 40° C. The reaction was allowed to proceed for 1.5 hour during which time the suspended solids changed from bright to pale yellow. The mixture was cooled by means of an ice bath and the solids were recovered by filtration on a sintered glass funnel, washed with 200 mL of chloroform, and dried to obtain 1.31 g (100 percent of theory) of the title compound as shiny pale yellow crystals melting at 183°–184° C.

Elemental Analysis $C_8H_8N_6S$ Calc.: % C, 43.8; % H, 3.57; % N, 38.4 Found: % C, 43.6; % H, 3.66; % N, 38.2

2. Preparation of 2-Benzylthio[1,2,4]triazolo[1,5-a]-pyrazine

A mixture of 1.94 g of imidazol-1-yl-N-(2-amino-1-pyrazinium) iminocarbothiolate, 50 mL of butanol, and 1.65 mL of benzyl chloride was heated to reflux with stirring for 1 hour. All of the solids dissolved and the mixture became dark. The volatiles were removed by evaporation under reduced pressure and the gummy residue was flash chromatographed on silica gel using a 0 to 2 percent gradient of ethanol and dichloromethane as the eluent. The eluent was removed by evaporation under reduced pressure to obtain 1.79 g of the title compound (84 percent of theory) as a gray-white solid melting at 93°–94° C.

Elemental Analysis $C_{12}H_{10}N_4S$ Calc.: % C, 59.1; % H, 4.27; % N, 23.2; % S, 13.6 Found: % C, 59.5; % H, 4.16; % N, 23.1; % S, 13.2

3. Preparation of 2-Benzylthio-5-bromo[1,2,4]triazolo-[1,5-a]pyrazine

A mixture of 10 mL of glacial acetic acid and 0.5 mL of acetic anhydride was refluxed for 10 min (minutes) to remove any water. 2-Benzylthio[1,2,4]triazolo[1,5-a]pyrazine (1.00 g) and then N-bromosuccinimide (0.91 g) were added to this at 50° C. with stirring. The mixture was monitored by thin layer chromatography for the presence of the benzylthio compound and additional N-bromosuccinimide was added until it disappeared, which required about 5 hours. The reaction became progressively more orange during the bromination. The mixture was poured into ice water and the resulting mixture was extracted with dichloromethane. The organic extract was washed sequentially with saturated aqueous sodium bicarbonate and water and was then dried over sodium sulfate and concentrated by evaporation under reduced pressure. The residue was flash chromatographed on silica gel eluting with a 0 to 1 percent gradient of ethanol and dichloromethane. The eluent was removed by evaporation under reduced pressure to obtain 0.70 g of the title compound (54 percent of theory) as a clear syrup which eventually solidified and melted at 94°–95° C.

Elemental Analysis $C_{12}H_9BrN_4S$ Calc.: % C, 44.9; % H, 3.07; % N, 17.4; % S, 9.81 Found: % C, 44.9; % H, 2.82; % N, 17.4; % S, 9.98

4. Preparation of 2-Benzylthio-5-methoxy[1,2,4]triazolo[1,5-a]pyrazine

2-Benzylthio-5-bromo[1,2,4]triazolo[1,5-a]pyrazine (0.71 g) was dissolved in 20 mL of methanol and to this 1.20 mL of 25 percent by weight solution of sodium methoxide in methanol was added by means of a syringe with stirring at ambient temperature. The mixture turned pale yellow and the reaction was complete in 4 hours. The mixture was quenched with 0.5 mL of glacial acetic acid and the volatiles were removed by evaporation under reduced pressure. The oily residue was triturated with water and the solid that formed was recovered by filtration to obtain 0.31 g (50 percent of theory) of the title compound as a light brown solid melting at 114°–116° C.

Elemental Analysis $C_{13}H_{12}N_4OS$ Calc.: % C, 57.3; % H, 4.44; % N, 20.6; % S, 11.8 Found: % C, 56.3; % H, 4.34; % N, 20.3; % S, 11.0

This solid was further purified by flash chromatography on silica gel eluting with a 1–2 percent gradient of ethanol and dichloromethane; a clear syrup which eventually crystallized was obtained.

5. Preparation of 2-Chlorosulfonyl-5-methoxy[1,2,4]triazolo[1,5-a]pyrazine

2-Benzylthio-5-methoxy[1,2,4]triazolo[1,5-a]pyrazine (0.31 g) was dissolved in 20 mL of dichloromethane and 20 mL of water was added. The mixture was cooled to 0° C. and chlorine gas was added in 5-sec shots with vigorous stirring and cooling until the starting material had disappeared as determined by high pressure liquid chromatography (HPLC). Excess chlorine was removed with nitrogen gas and the phases were separated. The aqueous phase was extracted with more dichloromethane. The coined organic phase and extract was dried over sodium sulfate and concentrated by evaporation under reduced pressure to obtain the title compound as a yellow solid. The nuclear magnetic resonance spectrum of this material was compatible with the structure assigned.

6. Preparation of N-(2,6-Dichlorophenyl)-5-methoxy-[1,2,4]triazolo[1,5-]pyrazine-2-sulfonamide The 2-chlorosulfonyl-5-methoxy[1,2,4]triazolo[1,5-a]pyrazine from Example 5 was dissolved in 10 mL of dry acetonitrile and to this was added sequentially with stirring at ambient temperature: 0.365 g of 2,6-dichloroaniline, 90 μL (microliters) of dry pyridine, and 8.0 μL of dimethyl sulfoxide. The reaction was complete in2 hours as determined by HPLC, and the mixture was an orange solution. The volatiles were removed by evaporation under reduced pressure and the residue was purified by flash chromatography on silica gel eluting with a 0 to 3 percent gradient of ethanol and dichloromethane to obtain 0.110 g (27 percent of theory for chloroxidation and condensation) of the title compound as a white crystalline solid melting at 194°–196° C.

Elemental Analysis $C_{12}H_9Cl_2N_5O_3S$ Calc.: % C, 38.5; % H, 2.42; % N, 18.7; % S, 8.57 Found: % C, 38.9; % H, 2.44; % N, 18.5; % S, 8.76

7. Preparation of 1,2,3-Triaminopyrazinium Mesitylenesulfonate

A suspension of 13.7 g (0.112 mol) 2,3-diaminopyrazine in 200 mL chloroform was cooled with an ice bath and stirred. A solution of 26 g (0.12 mol) o-mesitylenesulfonylhydroxylamine dissolved in 100 mL of chloroform was added rapidly, but dropwise to the slurry with an addition funnel. (Note - o-Mesitylenesulfonylhydroxylamine was prepared as described in *J. Org. Chem*, 38, 1239 (1973) except that for improved safety the crude damp filter cake was dissolved in chloroform, the residual water removed by decantation, and the resulting solution used directly.) The ice bath was removed after 30 min. The resulting dark mixture was filtered and the filter cake was washed with up to 500 mL of chilled chloroform and dried in a vacuum oven to obtain 28.8 g (79 percent of theory) of the title compound in crude form. A portion of this material was recrystallized from methanol and diethyl ether to obtain crystals melting at 232°–233° C. and the remainder was used without further purification.

Elemental Analysis $C_{13}H_{19}N_5O_3S$ Calc.: % C, 48.0; % H, 5.89; % N, 21.5; % S, 9.85 Found: % C, 47.4; % H, 6.65; % N, 20.7; % S, 9.74

8. Preparation of Imidazol-1-yl-N-(2,3-diamino-1-pyrazinium) Imincarbothiolate.

A suspension of 26.8 g (83 mmol) (millimole) of 1,2,3-triaminopyrazinium mesitylenesulfonate in 500 mL of chloroform was prepared and to this was added with stirring at room temperature, 20.1 g (102 mmol) of 90 percent 1,1'-thiocarbonyldiimidazole. The mixture was warmed to 50° C. and allowed to react for 1 hour. The resulting dark yellow slurry was filtered and the filter cake was washed with chilled chloroform until the filtrate was colorless. The filter cake was then dried under reduced pressure to obtain 17.3 g (89 percent of theory) of the title compound in crude form. A portion of this fine olive-brown powder was extracted with hot acetone to obtain a purified sample melting at 198°–199° C.

Elemental Analysis $C_8H_9N_7S$ Calc.: % C, 40.8; % H, 3.86; % N, 41.7; % S, 13.6 Found: % C, 41.4; % H, 3.92; % N, 41.0; % S, 12.5

9. Preparation of 8-Amino-2-benzylthio[1,2,4]triazolo[1,5-a]pyrazine

A suspension of 17.2 g (74 mmol) of imidazol-1-yl-N-(2,3-diamino-1-pyrazinium) iminocarbothiolate in 150 mL of butanol was combined with 10.0 mL (87 mmol) of benzyl chloride and the mixture was heated to reflux with stirring for 1 hour. The solid gradually dissolved and the mixture darkened. The solvent was removed by evaporation under reduced pressure using a rotary evaporator and then a vacuum oven. The resulting solid was then extracted repeatedly with hot acetone and the resulting murky extract was filtered through Celite® filtration aid. The filtrate was concentrated by evaporation under reduced pressure and the residue was further purified by flash column chromatography on silica gel using a 1 to 4 percent ethanol/dichloromethane gradient as eluent to obtain 11.7 g (62 percent of theory) of the title compound as a light yellow solid melting at 144°–145° C.

Elemental Analysis $C_{12}H_{11}N_5S$ Calc.: % C, 56.0; % H, 4.31; % N, 27.2; % S, 12.5 Found: % C, 55.7; % H, 4.37; % N, 27.2; % S, 12.7

10. Preparation of 8-Amino-2-benzylthio-5-bromo[1,2,4]-triazolo[1,5-a]pyrazine

A 140 mL aliquot of glacial acetic acid was dried by refluxing with 7 mL of acetic anhydride for several minutes and was then cooled to room temperature. A solution of 9.40 g (36.6 mmol) of 8-amino-2-benzylthio-[1,2,4]triazolo[1,5-a]pyrazine was prepared using this solvent. The solution was then stirred and treated portionwise with 7.18 g (40.3 mmol) of N-bromosuccinimide. After 30 min the solvent was removed by evaporation under reduced pressure and the syrupy orange residue was dissolved in 500 mL of dichloromethane. The resulting solution was washed with water, dried over sodium sulfate, and purified by flash column chromatography on silica gel using a 1 to 4 percent ethanol/dichloromethane gradient as eluent to obtain 6.61 g (54 percent of theory) of the title compound as a bright yellow solid melting at 149°–150° C.

Elemental Analysis $C_{12}H_{10}N_5BrS$ Calc.: % C, 42.9; % H, 3.00; % N, 20.8; % S, 9.54 Found: % C, 43.2; % H, 3.08; % N, 20.2; % S, 8.83

The 8-hydroxy analog of the title compound was also isolated from the column as a more polar by-product. It amounted to 1.70 g (14 percent of theory) and was a brown powder melting at 235°–240° C. (dec); mass spectrum, m/e 337 (M+1).

11. Preparation of 2-Benzylthio-8-bromo[1,2,4]triazolo[1,5-a]pyrazine and 2-Benzylthio-5,8-dibromo [1,2,4]triazolo[1,5-a]pyrazine A mixture of 8.67 g (33.7 mmol) of 8-amino-2-benzylthio [1,2,4]triazolo[1,5-a]pyrazine and 8.68 g (38.8 mmol) of cupric bromide was prepared in 300 mL of dry acetonitrile and was warmed to 60° C. under a nitrogen atmosphere. A solution of 6.1 mL (51 mmol) of t-butyl nitrite in 25 mL of dry acetonitrile was added with a syringe pump with stirring over 20 min. Gas evolution was evident in the dark mixture during the course of addition. Heating was continued for 15 min after the addition was complete and then the mixture was allowed to cool to room temperature. The resulting mixture was treated with 300 mL of saturated aqueous ammonium chloride and the layers were separated. The aqueous layer was washed with two portions of acetonitrile and the organic layers were combined, filtered and dried over sodium sulfate. The volatiles were removed by evaporation under reduced pressure and the resulting brown residue was purified by flash column chromatography on silica gel using a 0.5 to 2 percent ethanol/dichloromethane gradient as eluent to obtain 3.49 g (26 percent of theory) of the 5,8-dibromo title compound as a light yellow powder melting at 119°–121° C.

Elemental Analysis $C_{12}H_8N_4Br_2S$ Calc.: % C, 36.0; % H, 2.02; % N, 14.0; % S, 8.01 Found: % C, 36.2; % H, 2.12; % N, 13.8; % S, 8.05

In addition, 3.37 g (31 percent of theory) of the 8-bromo title compound was obtained as a light yellow powder melting at 114°–115° C.

Elemental Analysis $C_{12}H_9N_4BrS$ Calc.: % C, 44.9; % H, 2.82; % N, 17.4; % S, 10.0 Found: % C, 45.4; % H, 3.17; % N, 17.2; % S, 10.3

12. Preparation of 5,8-Dibromo-2-chlorosulfonyl[1,2,4]triazolo[1,5-a]pyrazine

A solution of 2.00 g (4.99 mmol) of 2-benzylthio-5,8-dibromo[1,2,4]triazolo[1,5-a]pyrazine was prepared in 40 mL of dichloromethane and was vigorously stirred with 50 mL (50 mmol) of 1M hydrochloric acid at 0° C. A 22.0 mL aliquot (17.4 mmol) of a 5.25 percent sodium hypochlorite solution (commercial bleach) was added dropwise to the agitated heterogeneous mixture. The volume of reagent necessary was determined by first adding the theoretical 3.0 equivalents required, then adding small aliquots until the intermediate sulfoxide was totally consumed. The slightly yellow reaction mixture was then quenched with a spatula tip of sodium sulfite and after a few minutes was allowed to warm to room temperature. The layers were separated and the aqueous layer was washed once with dichloromethane. The organic layers were combined, dried over sodium sulfate and concentrated by evaporation under reduced pressure. The resulting sticky solid was extracted with two portions of mixed hexanes and the residual solvent was removed by evaporation under reduced pressure at room temperature to obtain 1.62 g (87 percent of theory) of desired product as an off-white solid. This material was used without further analysis or purification.

13. Preparation of N-(2-Fluoro-6-methoxycarbonylphenyl)-5,8-dibromo[1,2,4]triazolo[1,5-a]pyrazine-2-sulfonamide A solution of 0.75 g (20 mmol) of 5,8-dibromo-2-chlorosulfonyl[1,2,4]triazolo[1,5-a]pyrazine in 8 mL of dry acetonitrile was placed in a flask equipped with a drying tube and was treated sequentially with 6.0 mL (6.0 mmol) of a 1M solution of N-trimethylsilyl-2-fluoro-6-methoxycarbonylaniline in acetonitrile and 25 μL (0.35 mmol) of dimethyl sulfoxide at room temperature with stirring. The reaction became progressively darker and after 1 hour, the volatiles were removed by evaporation under reduced pressure and the residue was dissolved in dichloromethane. The resulting solution was washed with water, dried over sodium sulfate, and concentrated by evaporation under reduced pressure. The residue was purified by flash column chromatography on silica gel using a 0.5 to 4 percent ethanol/dichloromethane gradient as eluent to obtain 715 mg (70 percent of theory) of the desired product as an orange glassy solid melting at 190°–195° C.; Mass Spectrum, m/e 510 (M+1).

14. Preparation of N-(2-Fluoro-6-methoxycarbonylphenyl)-5-bromo-8-methoxy[1,2,4]triazolo[1,5-a]pyrazine-2-sulfonamide A solution of 686 mg (1.35 mmol) of N-(2-fluoro-6-methoxycarbonylphenyl)-5,8-dibromo[1,2,4]triazolo-[1,5-a]pyrazine-2-sulfonamide in 10 mL dry acetonitrile was treated with 3.0 mL (3.0 mmol) of a 1M solution of sodium methoxide in dry methanol at 0° C. with stirring. The reaction was quenched after 5min with 0.5mL of glacial acetic acid and the volatiles were removed by evaporation under reduced pressure. The residue was triturated with water and the resulting light brown solid was collected by filtration and dried in a vacuum oven. This crude material was purified by flash column chromatography on silica gel using a 0.5 to 2percent ethanol/dichloromethane gradient as eluent to obtain 538 mg (87 percent of theory) of the title compound as a white glassy foam solid melting at 201°–202° C.

Elemental Analysis $C_{14}H_{11}N_5BrFO_5S$ Calc.: % C, 36.5; % H, 2.41; % N, 15.2; % S, 6.97 Found: % C, 36.6; % H, 2.39; % N, 14.9; % S, 7.02

15. Preparation of 2-Benzylthio-5-bromo-8-chloro[1,2,4]triazolo[1,5-a]pyrazine

A suspension of 1.04 g (3.08 mmol) of crude 2-benzylthio-5-bromo-8-hydroxy[1,2,4]triazolo[1,5-a]pyrazine in 40 mL of dry acetonitrile was prepared in a flask equipped with a condenser and a drying tube and to this was added with stirring 4.0mL (43mmol) of phosphorus oxychloride. The mixture was heated at reflux for 3 hours and the solvent was then removed by evaporation under reduced pressure. The dark residue was dissolved in dichloromethane and the resulting solution was washed with water and dried over sodium sulfate. The residue obtained after removal of the solvent by evaporation under reduced pressure was purified by flash column chromatography on silica gel using dichloromethane as the eluent to obtain 0.26 g (24 percent of theory) of the title compound as an off-white solid melting at 109°–110° C.

Elemental Analysis $C_{12}H_8N_4BrClS$ Calc.: % C, 40.5; % H, 2.27; % N 15.8; % S, 9.01 Found: % C, 40.3; % H, 2.13; % N, 15.5; % S, 8.62

16. Preparation of N-(2,6-Dichlorophenyl)-5,8-dimethoxy-[1,2,4]triazolo[1,5-a]pyrazine-2-sulfonamide A solution of 0.42 g (0.92 mmol) of N-(2,6-dichlorophenyl)-5-bromo-8-chloro[1,2,4]triazolo[1,5-a]-pyrazine-2-sulfonamide in 30 mL of dry acetonitrile was combined with 2.8 mL (5.6 mmol) of a 2M solution of sodium methoxide in methanol and the mixture was warmed to 40° C. under a nitrogen atmosphere with stirring. After 24 hours, the reaction was quenched with 1 mL of glacial acetic acid and the solvent was removed under reduced pressure. The residue was extracted portionwise with up to 100mL of tetrahydrofuran and the cloudy extract obtained was filtered and concentrated by evaporation under reduced pressure. The title compound was isolated from the residue obtained by flash column chromatography on silica gel using a 2 to 10 percent ethanol/dichloromethane gradient as eluent. The title compound, which was the least polar of the three compounds present, was further purified by extraction with warm methanol and diethyl ether mixtures to obtain 46 mg (12 percent of theory) as a white powder melting above 250° C. with decomposition.

Elemental Analysis $C_{13}H_{11}N_5Cl_2O_4S$ Calc.: % C, 38.6; % H, 2.74; % N, 17.3; % S, 7.93 Found: % C, 38.2; % H, 2.88; % N, 16.8; % S, 7.56

17. Preparation of 6-Bromo-2-chlorosulfonyl-8-methoxy-[1,2,4]triazolo[1,5-a]pyrazine A solution of 0.50 g (1.42 mmol) of 2-benzylthio-6-bromo-8-methoxy[1,2,4]triazolo[1,5-a]pyrazine was prepared in 20 mL of dichloromethane and 20 mL (20 mmol) of 1M hydrochloric acid was added to this with vigorous stirring at 0° C. An 8.1 mL aliquot (6.4 mmol) of a 5.25 percent sodium hypochlorite solution (commercial bleach) was added dropwise to the agitated heterogeneous mixture. The volume of reagent necessary was determined by first adding the theoretical 3.0 equivalents required, then adding small aliquots until the intermediate sulfoxide was totally consumed. The slightly yellow reaction mixture was then quenched with a spatula tip of sodium sulfite, and after a few minutes, was allowed to warm to room temperature. The layers were separated and the aqueous layer was washed once with dichloromethane. The organic layers were combined, dried over sodium sulfate, and concentrated by evaporation under reduced pressure. The resulting sticky solid was extracted with two portions of mixed hexanes and was then taken up in 50 mL of diethyl ether. The resulting solution was filtered through a cotton plug and the filtrate was concentrated by evaporation under reduced pressure at room temperature to obtain 0.37 g (80 percent of theory) of the title compound as a yellow syrup. This material was used without further analysis or purification.

18. Preparation of 3-Amino-2-fluoro-4-methylpyridine

To a solution of 10.1 g (65 mmol) of 2-fluoro-4-methyl-3-nitropyridine in 200 mL of ethyl acetate was added 25 g (0.40 mol) of acetic acid and 0.8 g of 5 percent palladium on carbon catalyst. This mixture was shaken under 50 psig (pounds per square inch gauge) (2400 kiloPascals) pressure of hydrogen for 18 hours, was filtered, and was concentrated by evaporation under reduced pressure to obtain an oil. This oil was partitioned between dilute aqueous sodium bicarbonate and ether. The organic phase was separated, dried over magnesium sulfate, and filtered. The filtrate was concentrated by evaporation under reduced pressure and the residue was purified by column chromatography to obtain 7.2 g (88 percent of theory) of the title compound as a colorless solid, melting at 63°–64° C. Nuclear Magnetic Resonance Spectrum (200 MHz (megaHertz), $CDC_{l3}$): $^1H$: 7.4 (d, 1H, J=5.0); 6.8 (d, 1H, J=5.0); 3.7 (br, 2H); 2.1 (s, 3H); $^{13}C$: 152.6 (d, J=229); 134.1 (d, J=8.6); 133.8 (d, J=14.5 ); 128.1 (d, J=27.1 ); 123.3, 16.4 (d, J=4.1).

19. Preparation of N-(2-Fluoro-4-methyl-3-pyridinyl)-6-bromo-8-methoxy[1,2,4]triazolo[1,5-a]pyrazine-2-sulfonamide A solution of 1.36 g (4.14 mmol) of 6-bromo-2-chlorosulfonyl-8-methoxy[1,2,4]triazolo[1,5-a]pyrazine in 15 mL of dry acetonitrile was placed in a flask equipped with a drying tube and was treated sequentially with 1.56 g (12.4 mmol) of 3-amino-2-fluoro-4-methylpyridine, 0.34 mL (4.21 mmol) of pyridine and 60 μL (0.85 mmol) of dimethyl sulfoxide at room temperature. The reaction became progressively darker and after 15 hours the volatiles were removed by evaporation under reduced pressure and the residue was dissolved in dichloromethane. The resulting solution was washed with four portions of 1M hydrochloric acid and one portion of water and was dried over sodium sulfate. The solvent was then removed by evaporation under reduced pressure and the residue obtained was purified by flash column chromatography on silica gel using a 0.5 to 4 percent ethanol/dichloromethane gradient as eluent. The solid obtained was further purified by extraction with diethyl ether to obtain 373 mg (22 percent of theory) of the desired product as an off-white powder melting at 210°–211° C. (dec); Mass Spectrum, m/e 417 (M+1).

Elemental Analysis $C_{12}H_{10}N_6BrFO_3S$ Calc.: % C, 34.6; % H, 2.42; % N, 20.1; % S, 7.68 Found: % C, 34.5; % H, 2.56; % N, 18.4; % S, 6.89

20. Preparation of 3-Amino-2-chloro-4-methoxypyridine

To a solution of 6.4 g (51 mmol) of 3-amino-4methoxypryidine in 30mL of 37 percent aqueous hydrochloric acid was slowly added 7.8 g of 30 percent aqueous hydrogen peroxide at room temperature with stirring. After 30 min this solution was slowly poured into 300 mL of saturated aqueous sodium bicarbonate and the resulting mixture was extracted with ether (3×200 mL). The ethereal extracts were combined, dried over magnesium sulfate, and filtered. The filtrate was concentrated by evaporation under reduced pressure to obtain a light brown solid. This solid was purified by column chromatography (17:83 acetone:hexane) to obtain 6.54 g (81 percent of theory) of the title compound as colorless needles melting at 86°–87° C.

Elemental Analysis $C_6H_7Cl\,N_2O$ Calc.: % C, 45.4; % H, 4.45; % N, 17.7 Found: % C, 45.4, % H, 4.65; % N, 17.8

Nuclear Magnetic Resonance Spectrum (200 MHz, $CDCl_3$): $^1H$: 7.7 (d, 1H, J=5.4); 6.6 (d, 1H, J=5.4), 4.0 (br, 2H); 3.8 (s, 3H); $^{13}C$: 153.3, 138.5, 135.6, 129.9, 105.2, 55.9.

21. Preparation of 3-Amino-4-fluoro-1-methylindazole

Methylhydrazine (4.96 g, 108 mmol) was added to a solution of 15.0 g (108 mmol) of 2,6-difluorobenzonitrile in 150 mL of ethanol and the mixture was heated to reflux with stirring for 72 hours. The volatiles were then removed by evaporation under reduced pressure and residue was dissolved in dichloromethane. The resulting solution was washed with water, dried over magnesium sulfate, and evaporated to dryness under reduced pressure to obtain a white solid. This was recrystallized from ethanol to obtain 10.1 g (57 percent of theory) of the title compound as white crystals melting at 125°–127° C.

Elemental Analysis $C_8H_8N_3F$ Calc.: % C, 58.2; % H, 4.88; % N, 25.4 Found: % C, 58.7, % H, 4.76; % N, 25.9

Nuclear Magnetic Resonance Spectrum (200 MHz, $CDCl_3$): $^1H$: 7.19 (m, 1H); 7.11 (d, 1H, J=8.4), 6.59 (d of d, 1H, J=8.4, 3.3), 5.26 (brs, 2H), 3.72 (s, 3H); $^{13}C$: 157.35, 154.88, 146.20, 146.18, 143.85, 143.76, 127.62, 127.55, 105.31, 105.27, 103.44, 103.24, 101.96, 101.78, 34.74.

22. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

24. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23°–29° C. during the day and 22°–28° C. during the night. Nutrients and water were added on a regular basis and supplemental lighting was provided with overhead metal halide 1000 Watt lamps as necessary. The water was added by top-irrigation. After 3 weeks the

TABLE 2

POSTEMERGENCE HERBICIDAL ACTIVITY

| Cpd. No. | Rate, ppm | Cocklebur | Jimsonweed | Lambsquarters | Morningglory | Velvetleaf | Veronica | Wild Buckwheat | Blackgrass | Johnsongrass |
|---|---|---|---|---|---|---|---|---|---|---|
| 1 | 250 | 90 | 78 | 50 | 78 | 100 | 40 | 70 | 0 | 0 |
| 2 | 2000 | 50 | 80 | 0 | 45 | 75 | — | 5 | 0 | 0 |
| 3 | 62.5 | 95 | 80 | 90 | 100 | 100 | 20 | 90 | 0 | 20 |
| 4 | 125 | 100 | 100 | 85 | 100 | 100 | 100 | 100 | 20 | 80 |
| 5 | 31.3 | 100 | 100 | 60 | 100 | 100 | 50 | 75 | 40 | 50 |
| 6 | 125 | 100 | 90 | 20 | 100 | 90 | 0 | 90 | 20 | 30 |
| 7 | 125 | 100 | 100 | 50 | 85 | 100 | 0 | 80 | 0 | 50 |
| 8 | 500 | 98 | 80 | 20 | 80 | 90 | 60 | 85 | 20 | 70 |
| 9 | 500 | 80 | 80 | 45 | 70 | 80 | 70 | 80 | 50 | 80 |
| 10 | 125 | 100 | 90 | 70 | 100 | 90 | 88 | 100 | 70 | 89 |
| 11 | 250 | 20 | 0 | 70 | 20 | 30 | 0 | 50 | 5 | 30 |
| 12 | 1000 | 55 | 70 | 0 | 70 | 60 | 20 | 30 | 20 | 50 |
| 13 | 62.5 | 100 | 100 | 30 | 100 | 95 | 100 | 100 | 15 | 75 |
|  | 7.8 | 90 | 80 | 0 | 95 | 85 | 70 | 100 | 0 | 60 |
| 14 | 62.5 | 90 | — | 60 | 95 | 85 | 90 | 95 | 50 | 60 |
| 15 | 62.5 | 90 | — | 60 | 90 | 100 | 95 | 100 | 70 | 80 |
| 16 | 31.3 | 100 | 88 | 90 | 95 | 90 | 100 | 95 | 60 | 90 |
|  | 3.9 | 90 | 87 | 70 | 100 | 88 | 80 | 88 | 25 | 75 |
| 17 | 3.9 | 100 | 97 | 40 | 95 | 97 | 70 | 40 | 0 | 35 |
| 18 | 15.6 | 100 | 75 | 65 | 83 | 90 | 85 | 70 | 15 | 20 |
| 19 | 15.6 | 100 | 90 | 75 | 75 | 85 | 80 | 70 | 20 | 30 |
| 20 | 250 | 90 | — | 90 | 90 | 90 | 85 | 90 | 50 | 70 |
| 21 | 31.3 | 100 | 97 | 80 | 80 | 80 | 30 | 83 | 60 | 80 |
| 23 | 500 | 40 | — | 40 | 70 | 40 | 95 | 88 | 40 | 30 |
| 24 | 500 | 85 | 80 | 20 | 70 | 10 | 80 | 0 | 0 | 60 | condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

PREEMERGENCE HERBICIDAL ACTIVITY

| Cpd. No. | Rate, Kg/Ha | Morning-glory | Pigweed | Velvet-leaf | Wild Buck-wheat | Black-grass | Barn-yard Grass | Johnson-grass |
|---|---|---|---|---|---|---|---|---|
| 3 | 1.12 | 90 | 85 | 98 | 85 | 50 | 85 | 90 |
| 4 | 0.28 | 90 | 98 | 95 | 75 | 20 | 80 | 75 |
| 5 | 0.56 | 90 | 100 | 90 | 90 | 75 | 90 | 85 |
| 6 | 1.12 | 90 | 50 | 90 | 80 | 50 | 90 | 90 |
| 7 | 1.12 | 90 | 20 | 85 | 50 | 30 | 80 | 55 |
| 9 | 0.56 | 80 | 50 | 85 | 30 | 50 | 60 | 75 |
| 10 | 0.28 | 90 | 100 | 100 | 95 | 85 | 100 | 65 |
| 13 | 0.56 | 90 | 100 | 90 | 90 | 60 | 100 | 98 |
| 14 | 0.28 | 90 | 98 | 95 | 95 | 50 | 75 | 80 |
| 15 | 0.070 | 90 | 98 | 95 | 90 | 75 | 90 | 90 |
| 16 | 0.14 | 80 | 90 | 80 | 60 | 70 | 95 | — |
| 17 | 0.14 | 90 | 98 | 95 | 80 | 100 | 50 | 95 |
| 18 | 0.035 | 80 | 98 | 85 | 80 | 100 | 75 | 85 |
| 20 | 0.28 | 90 | 95 | 80 | 90 | 70 | 70 | 80 |
| 21 | 0.070 | 90 | 98 | 90 | 90 | 75 | 60 | 90 |

What is claimed is:

1. An N-aryl[1,2,4]triazolo[1,5-a]pyrazine-2-sulfonamide compound of the formula:

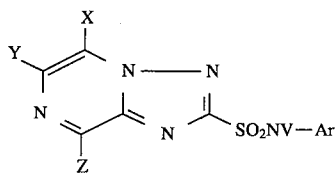

wherein

X, Y, and Z each independently represents H, $CH_3$, $CF_3$, F, Cl, Br, or $(C_1-C_3)$alkoxy;

V represents H, COR', $CO_2R''$, or $CONR'''_2$;

Ar represents an aromatic moiety of one of the formulas:

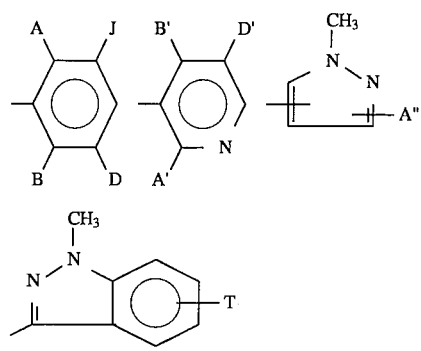

A represents F, Cl, Br, $CO_2R''$, $CONR'''_2$, $(C_1-C_2)$haloalkyl, $NO_2$, CN, SOR', or $SO_2R'$;

B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$, and $CH_3$;

D and J each independently represents H or $CH_3$ with the proviso that at least one of D and J represents H;

A' and B' each independently represents H, R', OR', $S(O)_nR'$, F, Cl, Br, I, CN, $NO_2$, $C_6H_5$, $CO_2R''$, or $CONR'''_2$ with the proviso that not more than one of A' and B' represents H;

D' represents H, F, Cl, Br, I, $CF_3$, or $CH_3$;

A" represents F, Cl, Br, I, $CF_3$, $SCF_3$, CN, $CO_2R''$, or $CONR'''_2$ and is located in the 4-position when the point of attachment is the 3- or 5-position and represents F, Cl, Br, I, $CF_3$, or $CH_3$ and is located in the 3- and/or 5-position when the point of attachment is the 5-position;

T represents H or F;

n represents 0, 1, or 2;

R' represents $(C_1-C_3)$alkyl optionally singly to completely substituted with fluorine;

R" represents $(C_1-C_4)$ alkyl, $(C_3-C_4)$ alkenyl, or $(C_3-C_4)$ alkynyl;

R''' represents H or $(C_1-C_4)$alkyl; and when V represents H, the agriculturally acceptable salts thereof.

2. A compound according to claim 1 wherein V represents H.

3. A compound according to claim 1 wherein at least one of X and Z represents $OCH_3$ or $OC_2H_5$.

4. A compound according to claim 1 wherein Ar represents substituted phenyl of the formula:

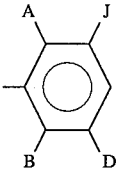

wherein A represents one of F, Cl, Br, $CO_2R''$, $NO_2$, and $CF_3$; B represents one of F, Cl, Br, $OCH_3$, and $CH_3$; J represents H, and D represents H or $CH_3$.

5. A compound according to claim 1 wherein Ar represents substituted 3-pyridinyl of the formula:

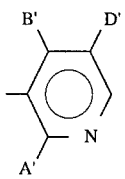

wherein A' represents Cl, F, or OCH$_3$; B' represents CH$_3$, OCH$_3$, OC$_2$H$_5$, OC$_3$H$_7$(n), or OC$_3$H$_7$(i); and D' represents H or wherein A' represents H, B' represents CO$_2$(C$_1$–C$_2$)alkyl, and D' represents H.

6. A compound according to claim 1 wherein Ar represents substituted 3-, 4-, or 5-pyrazolyl of the formula:

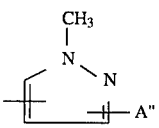

wherein A" represents Cl, Br, I or CF$_3$.

7. A compound according to claim 4 which is 5-bromo-N-(2,6-dichlorophenyl)-8-methoxy[1,2,4]triazolo[1,5-a]pyrazine-2-sulfonamide, 5-bromo-N-(2-fluoro-6-methoxycarbonylphenyl)-8-methoxy[1,2,4]triazolo[1,5-a]-pyrazine-2-sulfonamide, N-(2,6-dichlorophenyl)-5,8-dimethoxy[1,2,4]triazolo[1,5-a]pyrazine-2-sulfonamide, 6-chloro-N-(2,6-dichlorophenyl)-8-methoxy[1,2,4]triazolo-[1,5-a]pyrazine-2-sulfonamide, or 6-chloro-N-(2, 6-difluorophenyl)-8-methoxy [1,2,4]triazolo[1,5-a]pyrazine-2-sulfonamide, or an agriculturally acceptable salt thereof.

8. An herbicidal composition comprising an herbicidally effective amount of an N-aryl[1,2,4]triazolo[1,5-a]pyrazine-2-sulfonamide compound of the formula:

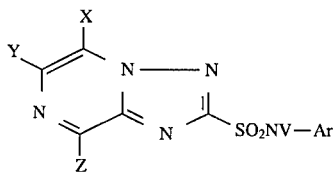

wherein

X, Y, and Z each independently represents H, CH$_3$, CF$_3$, F, Cl, Br, or (C$_1$–C$_3$)alkoxy;

V represents H, COR', CO$_2$R", or CONR'"$_2$;

Ar represents an aromatic moiety of one of the formulas:

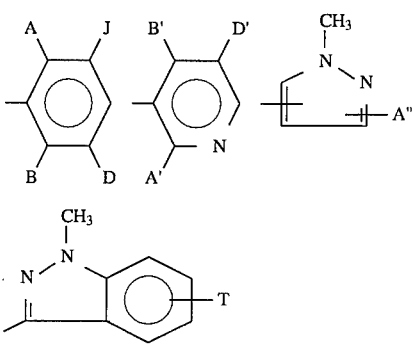

A represents F, Cl, Br, CO$_2$R", CONR'"$_2$, (C$_1$–C$_2$)haloalkyl, NO$_2$, CN, SOR', or SO$_2$R';

B represents H, CH$_3$, C$_2$H$_5$, F, Cl, Br, CN, OR', SR', NR'"$_2$, phenyl, or phenoxy, each phenyl and phenoxy optionally possessing 1 to 3 substituents selected from the group consisting of F, Cl, Br, CN, CF$_3$, NO$_2$, and CH$_3$;

D and J each independently represents H or CH$_3$ with the proviso that at least one of D and J represents H;

A' and B' each independently represents H, R', OR', S(O)$_n$R', F, Cl, Br, I, CN, NO$_2$, C$_6$H$_5$, CO$_2$R", or CONR'"$_2$ with the proviso that not more than one of A' and B' represents H;

D' represents H, F, Cl, Br, I, CF$_3$, or CH$_3$;

A" represents F, Cl, Br, I, CF$_3$, SCF$_3$, CN, CO$_2$R", or CONR'"$_2$ and is located in the 4-position when the point of attachment is the 3- or 5-position and represents F, Cl, Br, I, CF$_3$, or CH$_3$ and is located in the 3- and/or 5-position when the point of attachment is the 4-position;

T represents H or F;

n represents 0, 1, or 2;

R' represents (C$_1$–C$_3$)alkyl optionally singly to completely substituted with fluorine;

R" represents (C$_1$–C$_4$) alkyl, (C$_3$–C$_4$) alkenyl, or (C$_3$–C$_4$) alkynyl;

R'" represents H or (C$_1$–C$_4$)alkyl; and when V represents H, the agriculturally acceptable salts thereof in admixture with an agriculturally acceptable adjuvant or carrier.

9. A composition according to claim 8 wherein V represents H.

10. A composition according to claim 8 wherein at least one of X and Z represents OCH$_3$ or OC$_2$H$_5$.

11. A composition according to claim 8 wherein Ar represents substituted phenyl of the formula:

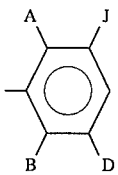

wherein A represents one of F, Cl, Br, CO$_2$R", NO$_2$, and CF$_3$; B represents one of F, Cl, Br, OCH$_3$, and CH$_3$; J represents H, and D represents H or CH$_3$.

12. A composition according to claim 8 wherein Ar represents substituted 3-pyridinyl of the formula:

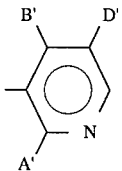

wherein A' represents Cl, F, or OCH$_3$; B' represents CH$_3$, OCH$_3$, OC$_2$H$_5$, OC$_3$H$_7$(n), or OC$_3$H$_7$(i); and D' represents H or wherein A' represents H, B' represents CO$_2$(C$_1$–C$_2$)alkyl, and D' represents H.

13. A composition according to claim 8 wherein Ar represents substituted 3-, 4-, or 5-pyrazolyl of the formula:

wherein A" represents Cl, Br, I, or $CF_3$.

14. A composition according to claim 11 wherein the compound is 5-bromo-N-(2,6-dichlorophenyl)-8-methoxy [1,2,4]triazolo[1,5-a]pyrazine-2-sulfonamide, 5-bromo-N-(2-fluoro-6-methoxycarbonylphenyl)-8-methoxy-[1,2,4]triazolo[1,5-a]pyrazine-2-sulfonamide, N-(2,6-dichlorophenyl)-5,8-dimethoxy [1,2,4]triazolo[1,5-a]pyrazine-2-sulfonamide, 6-chloro-N-(2,6-dichlorophenyl)-8-methoxy [1,2,4]triazolo[1,5-a]pyrazine-2-sulfonamide, or 6-chloro-N-(2,6-difluorophenyl)-8-methoxy [1,2,4]triazolo[1,5-a]pyrazine-2-sulfonamide, or an agriculturally acceptable salt thereof.

15. A method of controlling undesirable vegetation which comprises applying to said vegetation or to the locus thereof an herbicidally effective amount of an N-aryl[1,2,4]triazolo[1,5-a]pyrazine-2-sulfonamide compound of the formula:

wherein

X, Y, and Z each independently represents H, $CH_3$, $CF_3$, F, Cl, Br, or $(C_1-C_3)$alkoxy;

V represents H, COR', $CO_2R''$, or $CONR'''_2$;

Ar represents an aromatic moiety of one of the formulas:

A represents F, Cl, Br, $CO_2R''$, $CONR'''_2$, $(C_1-C_2)$haloalkyl, $NO_2$, CN, SOR', or $SO_2R'$;

B represents H, $CH_3$, $C_2H_5$, F, Cl, Br, CN, OR', SR', $NR'''_2$, phenyl, or phenoxy, each phenyl and phenoxy optionally possessing 1 to 3 substituents selected from the group consisting of F, Cl, Br, CN, $CF_3$, $NO_2$, and $CH_3$;

D and J each independently represents H or $CH_3$ with the proviso that at least one of D and J represents H;

A' and B' each independently represents H, R', OR', $S(O)_nR'$, F, Cl, Br, I, CN, $NO_2$, $C_6H_5$, $CO_2R''$, or $CONR'''_2$ with the proviso that not more than one of A' and B' represents H;

D' represents H, F, Cl, Br, I, $CF_3$, or $CH_3$;

A" represents F, Cl, Br, I, $CF_3$, $SCF_3$, CN, $CO_2R''$, or $CONR'''_2$ and is located in the 4-position when the point of attachment is the 3- or 5-position and represents F, Cl, Br, I, $CF_3$, or $CH_3$ and is located in the 3- and/or 5-position when the point of attachment is the 4-position;

T represents H or F;

n represents 0, 1, or 2;

R' represents $(C_1-C_3)$alkyl optionally singly to completely substituted with fluorine;

R" represents $(C_1-C_4)$alkyl, $(C_3-C_4)$alkenyl, or $(C_3-C_4)$alkynyl;

R''' represents H or $(C_1-C_4)$alkyl; and when V represents H, the agriculturally acceptable, salts thereof.

16. A method according to claim 15 wherein V represents H.

17. A method according to claim 15 wherein at least one of X and Z represents $OCH_3$ or $OC_2H_5$.

18. A method according to claim 15 wherein Ar represents substituted phenyl of the formula:

wherein A represents one of F, Cl, Br, $CO_2R''$, $NO_2$, and $CF_3$; B represents one of F, Cl, Br, $OCH_3$, and $CH_3$; J represents H, and D represents H or $CH_3$.

19. A method according to claim 15 wherein Ar represents substituted 3-pyridinyl of the formula:

wherein A' represents Cl, F, or $OCH_3$; B' represents $CH_3$, $OCH_3$, $OC_2H_5$, $OC_3H_7(n)$, or $OC_3H_7(i)$; and D' represents H or wherein A' represents H, B' represents $CO_2(C_1-C_2)$alkyl, and D' represents H.

20. A method according to claim 15, wherein Ar represents substituted 3-, 4-, or 5-pyrazolyl of the formula:

wherein A" represents Cl, Br, I, or $CF_3$.

21. A method according to claim 18 wherein the compound is 5-bromo-N-(2,6-dichlorophenyl)-8-methoxy[1,2,4]triazolo[1,5-a]pyrazine-2-sulfonamide, 5-bromo-N-(2-fluoro-6-methoxycarbonylphenyl)-8-methoxy [1,2,4]triazolo[1,5-a]pyrazine-2-sulfonamide, N-(2,6-dichlorophenyl)-5,8-dimethoxy [1,2,4]triazolo[1,5-a]pyrazine-2-sulfonamide, 6-chloro-N-(2,6-dichlorophenyl)-8-methoxy[1,2,4]triazolo[1,5-a]pyrazine-2-sulfonamide, or 6-chloro-N-(2,6-difluorophenyl)-8-methoxy [1,2,4]triazolo[1,5-a]pyrazine-2-sulfonamide, or an agriculturally acceptable salt thereof.

* * * * *